United States Patent [19]
Becherer et al.

[11] Patent Number: 5,393,894
[45] Date of Patent: Feb. 28, 1995

[54] PROCESS FOR THE PREPARATION OF N-ETHYLCARBAZOLE

[75] Inventors: Johannes Becherer, Maintal; Peter Koch, Obertshausen, both of Germany

[73] Assignee: Cassella Aktiengesellschaft, Frankfurt am Main, Germany

[21] Appl. No.: 275,594

[22] Filed: Jul. 15, 1994

[30] Foreign Application Priority Data

Jul. 23, 1993 [DE] Germany .............................. 4324707

[51] Int. Cl.$^6$ .......................................... C07D 209/86
[52] U.S. Cl. .................................................. 548/445
[58] Field of Search ........................................ 548/445

[56] References Cited

U.S. PATENT DOCUMENTS 3,346,573 10/1967 Fabricius ............................... 544/41
5,254,700 10/1993 Kamitamari et al. ............... 548/445

OTHER PUBLICATIONS

Lissel, Liebigs Ann. der Chemie, (1987) pp. 77–79.
Lissel, Synthesis, (1986) pp. 382–383.

Primary Examiner—Robert W. Ramsuer
Attorney, Agent, or Firm—Connolly & Hutz

[57] ABSTRACT

The present invention relates to a process for the preparation of N-ethylcarbazole by reaction of carbazole or N-ethoxycarbonylcarbazole with diethyl carbonate.

18 Claims, No Drawings

PROCESS FOR THE PREPARATION OF N-ETHYLCARBAZOLE

The present invention relates to a process for the preparation of N-ethylcarbazole of the formula I from a carbazole of the general formula II

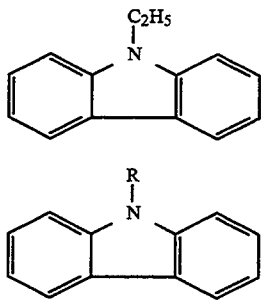

in which R denotes hydrogen or ethoxycarbonyl, by reaction with diethyl carbonate.

N-Ethylcarbazole is an important intermediate product for the preparation of valuable dyestuffs (compare Ullmanns Encyklopädie der technischen Chemie (Ullmann's Encyclopaedia of Industrial Chemistry), 3rd edition, Volume 5, page 80, 4th edition, Volume 9, page 120). It is prepared industrially by reaction of carbazole with potassium hydroxide or potassium carbonate to give the potassium salt of carbazole, which is then ethylated with an ethyl halide (see, for example, BIOS Final Report 986, page 197) or with diethyl sulphate (see, for example, DE-B-2132961). Other processes for the preparation of N-ethylcarbazole from carbazole use, for example, ethyl benzenesulphonate (Chemical Abstracts, Volume 82, Abstract No. 45003 (1975)), diethyl N-(o-tolyl)phosphoramidate (Journal of Heterocyclic Chemistry, Volume 18, page 315 (1981)) or 1,1-diethoxyethylium tetrafluoborate (Liebigs Annalen der Chemie, 1987, page 509), but these have no industrial importance.

The known industrial preparation processes all have the disadvantage that large amounts of inorganic salts are obtained, and have to be removed from the process waste waters by evaporation of the waste water in a labour- and energy-intensive manner and then have to be dumped, or which finally enter rivers with the waste waters via clarification plants. For example, if the process described in BIOS Final Report 986, page 197 is used, a waste water is obtained which comprises about 220 kg of potassium chloride per tonne of N-ethylcarbazole produced. By the process described in DE-B-2132961, as much as about 490 kg of potassium sulphate are to be found in the waste water per tonne of N-ethylcarbazole. The processes in which ethyl halides are used as ethylating agents also have the further disadvantage that a very expensive purification of the waste air must be carried out to avoid emission of organic halogen compounds, since simple combustion of the waste air is not possible because of the halogen content. A content of organic halogen compounds (AOX) in the waste water also cannot be avoided in these processes with aqueous working-up of the reaction mixture. Furthermore, both the use of ethyl halides and that of diethyl sulphate require particular measures when handling these substances because of the toxic and carcinogenic properties. An improved process for the preparation of N-ethylcarbazole would therefore be extremely desirable for both ecological and industrial hygiene reasons.

Instead of alkyl halides or dialkyl sulphates, dialkyl carbonates can in some cases be employed in alkylations of amines; thus, for example, the use of dimethyl carbonate in the presence of phase transfer catalysts, such as crown ethers, instead of dimethyl sulphate for methylation of imidazole is described in Liebigs Annalen der Chemie 1987, page 77. This publication refers to the pronounced difference in reactivity between dimethyl carbonate and diethyl carbonate, and in fact under no circumstances has a defined product been obtained with diethyl carbonate. The different behaviour of dimethyl and diethyl carbonate and the poorer results achieved with the latter are also discussed, for example, in Synthesis 1986, page 382. Ethylations on the nitrogen atom of amide groups by means of diethyl carbonate are possible; thus, European Patent Application EP-A-410214 mentions the reaction of urethanes with diethyl carbonate in the presence of at least equivalent amounts of alkali metal or alkaline earth metal carbonates and additionally phase transfer catalysts, but these reaction properties cannot be compared with those of amines because of the higher acidity of amides.

Diethyl carbonate in general reacts with amines to give carbamic acid esters (Houben-Weyl, Methoden der organischen Chemie (Methods of Organic Chemistry), Volume E 4, page 159; Ullmanns Encyklopädie der technischen Chemie (Ullmann's Encyclopaedia of Industrial Chemistry), 4th edition, Volume 14, page 591; see also DE-B-2160111), and ethylation is observed here only as a side reaction (U.S. Pat. No. 4,550,188).

Only in a few cases do ethylations occur as the main reaction in reactions of aromatic amines with diethyl carbonate. Thus, DE-A-2618033 also describes, in addition to reactions of various aniline derivatives with dimethyl carbonate, the reaction of p-phenylenediamine and p-toluidine, two monoarylamines activated by electron-donating substituents on the ring, with diethyl carbonate in which mixtures of products mono- and bisethylated on the nitrogen are formed. The gas phase reaction of aniline, a relatively highly volatile aromatic amine, with diethyl carbonate in the presence of a catalyst comprising polyethylene glycol and potassium carbonate gives a mixture of 56.5% of N-ethylaniline, 19.7% of N-ethoxycarbonyl-N-ethylaniline and 24.4% of aniline (Journal of Organic Chemistry, Volume 52, page 1300 (1987)), that is to say a high proportion of unreacted starting material. This method cannot be applied to amines of low volatility. Alkylation of aromatic amines by means of dialkyl carbonates in the presence of organic iodides as catalysts is mentioned in German Patent Specification DE-C-3007196. However, because of the addition of organic iodides, industrial realization of this process would again necessitate expensive purification of waste air and, with aqueous working-up, would lead to a content of organic halogen compounds in the waste water. Furthermore, only reactions with dimethyl carbonate, from which mixtures of N-methyl- and N,N-dimethylanilines are obtained, are disclosed. There are no indications that diethyl carbonate gives results similar to those with dimethyl carbonate, which as is known—as already mentioned above—has a substantially better alkylating action. The markedly different alkylation capacity of methyl and ethyl groups in carbonic acid esters can also be seen from EP-B-104601. That publication also mentions the use, in addition to the use of dimethyl carbonate, of mixed carbonic acid esters with a methyl group and a higher alkyl group, for example, and preferably, an ethyl group, for N-methylation of bis(2,4,6-tribromophenyl)amine to give the desired N,N-bis(2,4,6-tribromophenyl)methylamine. Alkylation proceeding alongside the methylation, in particular ethylation, which would indicate comparable reaction properties of the methyl and ethyl group in this type of reaction of N-alkylation of a diarylamine, is not referred to.

However, even with dimethyl carbonate, the reaction is also not complete, so that separation of educt and product becomes necessary.

Finally, DE-C-1195756 describes the reaction of aromatic-heterocyclic secondary amines, for example carbazole, with bis(dialkylaminoalkyl)carbonates. The peculiarities of this reaction are mentioned expressly, and in particular it is found that this specific alkylation method is not generally applicable to esters of carbonic acid, but is applicable specifically to the carbonic acid esters of those aliphatic alcohols which carry a tertiary amino group in the 2- or 3-position. This amino group probably attacks the alcohol carbon atom intermediately, and by this participation in the reaction is probably decisive for the properties observed. Correspondingly, here also no ethylation is found with the mixed carbonic acid ester of 3-dimethylaminopropanol and ethanol.

In view of the prior art described for the ethylation of amines with diethyl carbonate, it must be regarded as exceptionally surprising that it has now been possible to achieve the object of providing a simple new industrial preparation process for N-ethylcarbazole which avoids the abovementioned ecological and industrial hygiene disadvantages of the known processes by reacting carbazole or also N-ethoxycarbonylcarbazole with diethyl carbonate. The present invention thus relates to a process for the preparation of N-ethylcarbazole of the formula I

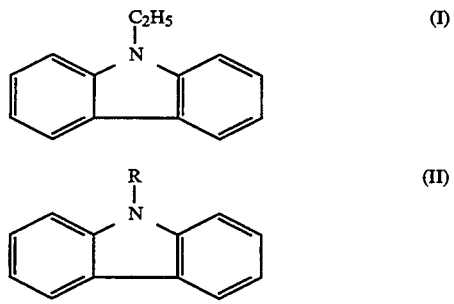

characterized in that a carbazole of the general formula II, in which R denotes hydrogen or ethoxycarbonyl, is reacted with diethyl carbonate.

Only carbon dioxide and ethanol are obtained as organic by-products in the process according to the invention. In addition to carbon dioxide, the waste air comprises ethanol and diethyl carbonate, which can easily be removed therefrom by means of a water washer or by waste air combustion. The organic compounds which have been washed out are halogen-free and very readily biologically degradable, so that the washer contents can easily be disposed of via any biological waste water purification plant. The toxicity of diethyl carbonate is significantly lower than, for example, that of diethyl sulphate, and the carcinogenic potential is lower. Compared with ethyl chloride, diethyl carbonate furthermore has the industrial hygiene advantage of a lower volatility. The smooth and complete course of the reaction, which produces a clean product, which can be employed in subsequent stages without an additional purification operation, in an excellent yield and in a high space/time yield furthermore is an advantage of the process according to the invention.

The process according to the invention can be carried out in a manner such that the carbazole derivative of the general formula II is reacted with diethyl carbonate without further additives, for example by heating at the desired temperature and with the desired reaction procedure. However, the reaction can also be carried out in the presence of additives. Thus, for example, in the case where R represents hydrogen, the carbazole of the general formula II can be converted into its salt by addition of an at least equivalent amount of a suitable base (or in this case, instead of the carbazole of the general formula II, a previously prepared salt can be reacted with the diethyl carbonate). According to the invention, however, the reaction can also be carried out, for example, in the presence of an amount of an added base which is smaller than the equivalent amount, that is to say without complete conversion of the carbazole of the general formula II, in which R represents hydrogen, into its salt. The course of the reaction is already influenced favourably by catalytic amounts of basic compounds. In a preferred embodiment, the reaction according to the invention of the substances of the general formula II is thus carried out under base catalysis. A large number of inorganic and organic basic compounds are suitable as the catalyst by themselves or as a mixture with other bases.

Examples of suitable bases, which indicate the wide range of compounds which can be employed, are lithium hydride, sodium hydride, potassium hydride, magnesium hydride, calcium hydride, methyllithium, butyllithium, phenyllithium, organomagnesium halides, dimsylsodium, tetraalkyl- and aralkyltrialkylammonium hydroxides, such as tetramethyl-, tetraethyl-, tetrabutyl-, benzyltrimethyl- or benzyltriethylaammonium hydroxide, salts of carboxylic acids, such as sodium acetate, potassium acetate, lithium acetate, sodium propionate, potassium propionate, sodium benzoate, potassium benzoate and potassium phthalate, organic nitrogen compounds, for example imidazoles, such as alkylimidazoles, for example methylimidazole, or diazabicyclononene or diazabicycloundecene, lanthanum hydroxide, lanthanum oxide, lanthanum carbonate, lithium borates, sodium borates and potassium borates, lithium silicates, sodium silicates and potassium silicates, basic ion exchangers and polymers which contain pyridyl radicals and have been prepared using vinylpyridines.

Particularly preferred catalysts are tertiary amines, pyridine derivatives, alkali metal salts of amines, alkali metal or alkaline earth metal salts of carbazole, alkali metal alcoholates, alkaline earth metal alcoholates or hydroxides, oxides, carbonates or phosphates of the alkali metals or alkaline earth metals or mixtures of these substances.

Tertiary amines used as the catalyst can contain branched and unbranched aliphatic, cycloaliphatic, araliphatic or aromatic radicals, for example methyl, ethyl, n-propyl, i-propyl, n-butyl, i-butyl, hexyl, octyl, decyl, dodecyl, hexadecyl, octadecyl, cyclopentyl, cyclohexyl, benzyl, phenethyl, phenyl, naphthyl and biphenyl radicals, in which carbon atoms can also be replaced by nitrogen or oxygen atoms and which can also contain substituents, such as alkyl groups or alkoxy groups or further tertiary amino groups. The nitrogen atom of the tertiary amine can also be a constituent of rings, for example of five- or six-membered rings or of bicyclic or tricyclic systems. Examples of suitable tertiary amines are trialkylamines, such as triethylamine, tributylamine, trioctylamine, tridecylamine, ethyldiisopropylamine or decyldimethylamine, aralkylamines, such as benzyldimethylamine or benzyldiethylamine, aryldialkylamines, such as N,N-dimethylaniline, N,N-diethylaniline or N,N-dibutylaniline, amines which are further substituted, such as N,N,N',N'-tetramethylethylenediamine, N,N,N',N'-tetramethylpropylenediamine, 1,8-bis(dimethylamino)naphthalene or tris(2-((2-methoxy)ethoxy)ethyl)amine, or cyclic amines, such as N-methylpyrrolidine, N-ethylpyrrolidine, N-phenylpyrrolidine, N-ethylpiperidine, 1,2,2,6,6-pentamethylpiperidine, N-ethylmorpholine or 1,4-diazabicyclo(2,2,-2)octane.

Pyridine derivatives which can be employed are, for example, pyridine itself or substituted pyridines, such as the picolines or lutidines, or such as 4-dimethylaminopyridine or fused pyridines, such as quinoline, quinaldine, acridine or 9-dimethylaminoacridine, or such as phenanthrolines, for example 1,10-phenanthroline.

Examples of alkali metal salts of amines which can be employed as catalysts are sodium amide, potassium amide, lithium amide, lithium, sodium and potassium dimethyl-, diethyl-, diisopropyl- and bistrimethylsilylamide, potassium(3-aminopropyl)amide or lithiumcyclohexylamide, and examples of alkali metal or alkaline earth metal salts of carbazole which can be employed as basic catalysts are the lithium salt, the sodium salt, the potassium salt, the caesium salt, the magnesium salt, the calcium salt or the barium salt of carbazole.

If alkali metal alcoholates or alkaline earth metal alcoholates are employed as catalysts, they can contain, as the metal, for example, lithium, sodium, potassium, caesium, magnesium, calcium or barium and can be derived from primary, secondary or tertiary alcohols, for example from methanol, ethanol, n-propanol, i-propanol, n-butanol, i-butanol, tert-butanol, amyl alcohols, benzyl alcohol, cyclopentanol or cyclohexanol, or also polyhydric alcohols, such as ethylene glycol, propylene glycol or also polyethylene glycols or polypropylene glycols. Suitable alcoholates are thus, for example, lithium methylate, sodium methylate, potassium methylate, magnesium methylate, calcium methylate, barium methylate, lithium ethylate, sodium ethylate, potassium ethylate, caesium ethylate, magnesium ethylate, calcium ethylate, barium ethylate, lithium isopropylate, sodium isopropylate, potassium isopropylate, lithium tert-butylate, sodium tert-butylate or potassium tert-butylate.

Examples of hydroxides, oxides, carbonates and phosphates of the alkali metals or alkaline earth metals which can be used as catalysts are lithium hydroxide, lithium oxide, lithium carbonate, lithium phosphate, sodium hydroxide, sodium oxide, sodium carbonate, sodium bicarbonate, sodium phosphate, potassium hydroxide, potassium oxide, potassium carbonate, potassium bicarbonate, potassium phosphate, caesium hydroxide, caesium carbonate, magnesium hydroxide, magnesium oxide, magnesium carbonate, magnesium hydroxide carbonate, magnesium phosphate, calcium hydroxide, calcium oxide, calcium carbonate, calcium phosphate, barium hydroxide, barium oxide, barium carbonate and barium phosphate, phosphates being understood as basic salts of monophosphoric acid, of diphosphoric acid and of polyphosphoric acids in which only some or all of the hydrogen atoms are replaced by the alkali metals or alkaline earth metals. The compounds mentioned can be employed in the anhydrous form, in the water-containing form, for example in the form of their hydrates, or also as a solution.

The amount of catalyst added depends on its catalytic activity and on the other reaction parameters chosen and can be varied within wide limits. Relatively large amounts of catalyst do not harm the reaction. As already mentioned, it is also possible to add bases in equivalent amounts, but an excess can also be used. It is thus also possible for the bases having a catalytic action to be used simultaneously as solvents. The catalyst is preferably employed in an amount of 0.05 to 20 mol percent, based on the carbazole of the general formula II employed. A catalyst amount of 0.1 to 10 mol percent is particularly preferred. If inorganic bases are used and if the catalyst is not re-used, these amounts lead in an ecologically advantageous manner to only a small amount of inorganic salts being obtained as a by-product.

The temperature at which the carbazole derivative of the general formula II is reacted with diethyl carbonate depends on the catalyst added and on the reaction medium. If suitable bases or base mixtures are added, the reaction can already proceed at room temperature or by heating to, for example, 130° C. The reaction is preferably carried out between 130° C. and 320° C. For example, if pyridine derivatives are employed as catalysts, the reaction can be carried out at lower temperatures. The reaction according to the invention is particularly preferably carried out between 180° and 300° C., and moreover preferably between 220° and 280° C.

The reaction can be carried out under superatmospheric pressure, it being possible for a certain superatmospheric pressure, for example a superatmospheric pressure of not more than 3 bar or not more than 6 bar, to be maintained in a controlled manner by means of a pressure-holding valve, or it being possible for the reaction to be carried out under the pressure which is established, for example, especially if low-boiling solvents are used, also under a high pressure in an autoclave. The reaction of the carbazole derivative of the general formula II with diethyl carbonate is preferably carried out under atmospheric pressure or under a superatmospheric pressure of not more than 3 bar.

The reaction can be carried out in a solvent or without a solvent. If no solvent is used, the carbazole of the general formula II is reacted with the amount of diethyl carbonate to be employed for conversion into the ethylcarbazole of the formula I and if appropriate with the addition of basic catalysts, at the desired temperature. If an amount of diethyl carbonate greater than that required for the conversion is added, this excess also functions as a solvent. When the reaction has ended, the excess diethyl carbonate can be recovered and re-used. All compounds which are stable under the reaction conditions at the desired temperature and towards the basic catalyst optionally added can otherwise be employed as solvents, for example aliphatic and aromatic hydrocarbons, such as, for example, benzine fractions, toluene and xylene, and also chlorohydrocarbons, such as chlorobenzene or o-dichlorobenzene, ethers, such as, for example, dibutyl ether, ethylene glycol ethers, such as diethylene glycol dimethyl ether or triethylene glycol dimethyl ether, dioxane, aza-aromatics, such as pyridine, picolines, lutidines and quinoline, these substances at the same time acting as basic catalysts, amides, such as dimethylformamide or N-methylpyrrolidone, or, for example, dimethyl sulphoxide or sulpholane. Molten N-ethylcarbazole can also advantageously be used as the solvent and can be isolated again together with the newly formed N-ethylcarbazole when the reaction has ended. The solvent can also be a mixture of two or more components.

The process according to the invention can be carried out in a manner such that the carbazole of the general formula II is kept at the desired temperature with the diethyl carbonate and, if appropriate, a basic catalyst and, if appropriate, a solvent until the content of carbazole of the general formula II, based on the N-ethylcarbazole, is below a desired limit value, for example below 1% or below 0.1%. Carbon dioxide is liberated during the reaction. The ethanol liberated during the reaction can be distilled out of the reaction mixture. The reaction temperature required and the reaction time depend on the nature and amount of the catalyst. If the reaction temperature is above the boiling point of the solvent or reaction mixture, the reaction must be carried out under pressure. If the reaction is carried out above the boiling point of diethyl carbonate, the ethanol is advantageously distilled off over a separating column or a partial condenser, the temperature of which is chosen such that boiling diethyl carbonate flows back into the batch but the vapours of ethanol formed can pass through the condenser. The ethanol vapours and, if appropriate, entrained diethyl carbonate are condensed in a subsequent condenser, it being possible, if appropriate, for this distillate also to be broken down by distillation into re-usable diethyl carbonate and ethanol which can be utilised elsewhere.

In a preferred embodiment of the process according to the invention, only some of the amount of diethyl carbonate, for example 5–50%, is initially introduced into the reaction vessel with the carbazole of the general formula II, if appropriate a catalyst and if appropriate a solvent, and the remaining amount is only metered in gradually at the reaction temperature at the rate at which it is consumed, or only the carbazole of the general formula II, if appropriate a catalyst and if appropriate a solvent are introduced into the reaction vessel and all the diethyl carbonate is gradually metered in at the reaction temperature, it being possible for the reflux from a reflux condenser operated at a suitable temperature to serve as a measure of the consumption if the reaction is carried out above the boiling point of diethyl carbonate.

When the reaction has ended, working up can be carried out in a manner such that, if appropriate, solid catalysts are filtered off at a suitable temperature and/or, if appropriate, volatile constituents, such as solvents, volatile catalysts, diethyl carbonate and ethanol, are separated off by distillation under a suitable pressure, for example under atmospheric pressure or in vacuo. The product which remains can in general be used directly for further processing. If required, if appropriate, it can be freed from small amounts of salts again by filtration of the melt, or also purified, for example by extraction, for example by extraction of salts from the product with hot water, by crystallization or by distillation. The diethyl carbonate recovered and the solvent and the catalyst recovered can be re-used in the following batch.

The process according to the invention for the preparation of N-ethylcarbazole is preferably carried out such that carbazole of the formula IIa

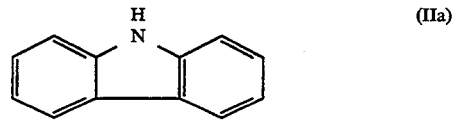

is reacted with diethyl carbonate, hydroxides, oxides, carbonates, phosphates or ethylates of alkali metals or of alkaline earth metals or the salts formed by these metals with carbazole or mixtures of these compounds being employed as the catalyst and the reaction being carried out in molten N-ethylcarbazole or in diethyl carbonate or in a mixture thereof. The use of the catalysts mentioned, for which examples have already been listed and which can be recovered by filtration after the reaction, has the particular advantage over the use of other basic organic compounds, which could likewise serve as catalysts, that at the end, in addition to the product and the volatile components ethanol and diethyl carbonate, which are automatically obtained and can easily be separated off by distillation, and possible non-interfering impurities originating from the carbazole employed, the reaction mixture contains no additional organic constituents. This saves relatively expensive working-up and purification operations. For the same reason, the use of N-ethylcarbazole or of diethyl carbonate, which is then thus employed in excess, as the reaction medium is also particularly advantageous. Other solvents in which the reaction could also be carried out would require a greater expenditure on reprocessing. In the particularly preferred procedure in which N-ethylcarbazole is used as the reaction medium, it is also possible, when the reaction has ended, to draw off from the ethylation vessel and work up only some, for example 30–70%, preferably 50–70%, of the reaction mixture, while the remainder remains in the ethylation vessel as the reaction medium for the next batch. By allowing the catalyst to settle before removal of the portion of the reaction mixture envisaged for working-up, the catalyst can thereby be largely kept in the reaction vessel and therefore be used several times, which reduces the amount of salt in the waste water still further.

Of the catalysts mentioned for this preferred embodiment, in which carbazole of the formula IIa is reacted with diethyl carbonate, potassium hydroxide, potassium carbonate and potassium ethylate are particularly preferred, especially potassium hydroxide and potassium carbonate, in each case by themselves or as a mixture with one another. The preferred embodiment is particularly preferably carried out in the temperature range between 130° and 320° C., especially preferably between 180° and 300° C. and in particular between 220° and 280° C. In the preferred embodiment, the diethyl carbonate is advantageously employed in excess, even if N-ethylcarbazole is used as the reaction medium, particularly preferably in an amount of 1.1 to 2.5 mol, especially preferably 1.1 to 1.8 mol, based on the carbazole of the formula IIa employed. The portion which has not been consumed can be recovered by distillation after the reaction has ended.

The process according to the invention for the preparation of N-ethylcarbazole is furthermore preferably carried out such that N-ethoxycarbonylcarbazole of the formula IIb

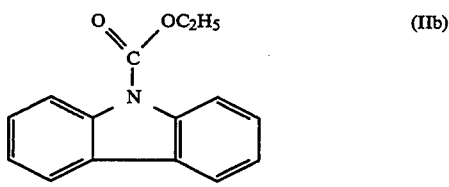

is reacted with diethyl carbonate, the diethyl carbonate being employed in an amount of 0.1 to 1 mol, preferably 0.3 to 0.8 mol, based on the carbazole of the formula IIb employed, and the reaction being carried out without an additional solvent. In the particularly preferred procedure of this embodiment, which is carried out under basic catalysis, the considerations already put forward apply accordingly to selection of the catalyst. Here also, the preferred procedure for the reaction in a melt of N-ethoxycarbonylcarbazole or in diethyl carbonate, dispensing with an additional solvent in which the reaction could also be carried out, saves a relatively high expenditure on working-up. The preparation of the starting substance of this preferred embodiment, N-ethoxycarbonylcarbazole, is described in U.S. Pat. No. 2,089,985.

The following examples serve to illustrate the process according to the invention.

EXAMPLE 1:

81 g of N-ethylcarbazole, industrial 96.5% pure goods, are melted in a 250 ml multi-necked flask with a reflux condenser which is operated with water at 90° C. and onto which a Liebig condenser operated with ice-water is mounted. 69.5 g of carbazole, 96% pure technical grade, and 3 g of potassium methylate are introduced at a temperature of 100°–130° C., while stirring thoroughly. The suspension is heated up to 230°–240° C. in the course of one hour, dropwise addition of diethyl carbonate being started at an internal temperature of 180°–200° C. The internal temperature is kept at 230°–240° C. for 24 hours and diethyl carbonate is added dropwise at a rate such that it boils constantly under reflux. Overall, about 70 g are consumed. During the reaction, carbon dioxide escapes and ethanol, contaminated with a little diethyl carbonate and methanol, distils off. As soon as the reaction has ended, the excess diethyl carbonate is distilled off by application of a vacuum and the product melt which remains is extracted by stirring with water at temperatures of 70°–100° C. After the organic phase has been dried by evaporation of the residual moisture, 161 g of N-ethylcarbazole, 96% pure, are obtained, which, taking into account the amount employed, corresponds to a yield of 98% of theory. After neutralization with hydrochloric acid, the waste water contains 3.2 g of potassium chloride, which corresponds to 42 kg of potassium chloride per tonne of N-ethylcarbazole prepared.

EXAMPLE 2:

If the procedure is as in Example 1, but the batch is freed from the catalyst by filtration of the product melt at temperatures of about 100° C., 158 g of N-ethylcarbazole, 96% pure, are obtained, which, taking into account the amount employed, corresponds to a yield of 95%. The product which adheres to the residue on the filter is not taken into account here.

EXAMPLE 3:

If the procedure is as in Example 1, but instead of potassium methylate, 4 g of potassium tert-butylate are added as the catalyst, N-ethylcarbazole is obtained in the same yield and quality.

EXAMPLE 4:

If the procedure is as in Example 1, but, instead of potassium methylate, 7 g of the potassium salt of carbazole are added as the catalyst at a reaction temperature of 250°–260° C., 162 g of N-ethylcarbazole are obtained in a purity of 96.5% after a reaction time of 20 hours.

EXAMPLE 5:

If the procedure is as in Example 1, but, instead of potassium methylate, 2 g of 4-dimethylaminopyridine are added as the catalyst and the mixture is heated at 160°–170° C. for 24 hours and worked up by vacuum distillation, after a first running which comprises dimethylaminopyridine and N-ethylcarbazole and can be re-used, if appropriate, in a subsequent batch has been removed, 155 g of 96% pure N-ethylcarbazole are obtained, which corresponds to a yield of 91%, not taking into account the product contained in the first running.

EXAMPLE 6:

50 ml of o-dichlorobenzene are initially introduced into the apparatus described in Example 1, and 35 g of carbazole, 96% pure, are introduced and dissolved. 36 g of diethyl carbonate and 1 g of 4-dimethylaminopyridine are added and the entire mixture is heated under reflux. An internal temperature of about 150° C. is established, and rises to about 167°–170° C. in the course of time. After about 24 hours, 1 g of catalyst is subsequently added. After 48 hours under reflux, the reaction has ended and the mixture can be worked up by distillation analogously to Example 5.

EXAMPLE 7:

If the procedure is as in Example 4, but, instead of the potassium salt of carbazole, 5 g of N,N-dimethylaniline is added as the catalyst, the reaction has ended after about 40 hours.

EXAMPLE 8:

If the procedure is as in Example 1, but is carried out entirely without the addition of a catalyst and at temperatures of 270°–310° C., the reaction has ended after about 40 hours.

EXAMPLE 9:

505 g of N-ethylcarbazole, industrial 96.5% pure goods, are melted in a 2 l multi-necked flask with a reflux condenser which is operated with water at 90° C. and onto which a Liebig condenser operated with ice-water is mounted. 1044 g of carbazole, industrial 96% pure goods, and 30 g of potassium hydroxide, 90% pure, are introduced at a temperature of 100°–130° C., while stirring thoroughly. The suspension is heated up to 230°–240° C. in the course of one hour, dropwise addition of diethyl carbonate being started at an internal temperature of 180°–200° C. The internal temperature is kept at 230°–240° C. for 24 hours and diethyl carbonate is added dropwise at a rate such that it boils constantly under reflux. Overall, about 1000 g are consumed. During the reaction, carbon dioxide escapes and ethanol distils off with a little diethyl carbonate. As soon as the reaction has ended, the excess diethyl carbonate is distilled off by application of a vacuum and the product melt which remains is freed from the catalyst by filtration at temperatures of about 100° C. The residue on the filter is treated with hot water, the inorganic constituents potassium hydroxide and potassium carbonate dissolving. Adhering product is either separated off hot as an organic phase or isolated by filtration after cooling. A total of 1706 g of N-ethylcarbazole, 96.5% pure, are obtained, 1630 g of which as a filtered melt and the remainder from the aqueous working-up of the residue on the filter, which, taking into account the amount employed, is a yield of 99%. The product contains as impurities only the secondary components which were already contained in the industrial carbazole.

After neutralization with hydrochloric acid, the waste water obtained from working up the residue on the filter contains about 36 g of potassium chloride, which corresponds to 31 kg per tonne of N-ethylcarbazole, 100% pure, prepared.

EXAMPLE 10:

The procedure is as in Example 9, but 500 g of N-ethylcarbazole, 800 g of carbazole and 2.5 g of potassium hydroxide are employed instead of 505 g of N-ethylcarbazole, 1044 g of carbazole and 30 g of potassium hydroxide. The internal temperature is kept at 230°–240° C. for only about 4 hours and is then increased to 260°–270° C. About 650 g of diethyl carbonate are consumed. The reaction has ended about 16 hours after the start of the addition of diethyl carbonate. After working up as in Example 9, 1420 g of N-ethylcarbazole, 96.5% pure, are obtained, 1415 g thereof as filtered melt. The neutralized waste water contains about 3 g of potassium chloride, which corresponds to about 3–4 kg per tonne of N-ethylcarbazole, 100% pure, prepared.

EXAMPLE 11:

A batch was initially carried out analogously to Example 10, but with 10 g of potassium hydroxide as the catalyst. When the reaction had ended, the stirrer was switched off and the catalyst was allowed to settle. The reaction mixture was then siphoned off from the flask down to 500 g and worked up.

The crude mixture remaining in the flask, including the catalyst, was used as the reaction medium for the next batch, in which the procedure was again as above. Five subsequent batches in total were carried out in this manner without further addition of catalyst. Up to this point in time, still no reduction in catalyst activity was to be found.

The average amount of salt obtained up until then is 2–2.5 kg of potassium chloride per tonne of N-ethylcarbazole or the corresponding amount of a mixture of potassium hydroxide and potassium carbonate, if the waste water is not neutralized with hydrochloric acid. The average amount of salt obtained per tonne of product can be further reduced by further subsequent batches until there is a detectable reduction in catalyst activity.

EXAMPLE 12:

If the procedure is as in Example 10, but only 0.3 g of potassium hydroxide is employed as the catalyst, the reaction takes about 30 hours until the reaction is complete, at the same yield and product quality. The amount of salt obtained is less than 0.5 kg per tonne of N-ethylcarbazole.

EXAMPLE 13:

If the procedure is as in Example 9, but is carried out at a reaction temperature of 260°–270° C. and 60 g of potassium carbonate are employed as the catalyst instead of potassium hydroxide, N-ethylcarbazole is obtained in the same yield and quality after a reaction time of 20 hours.

EXAMPLE 14:

If the procedure is as in Example 4, but 3 g of tripotassium phosphate are employed as the catalyst, the reaction has ended after about 50 hours.

EXAMPLE 15:

If the procedure is as in Example 4, but 12 g of barium hydroxide octahydrate are employed as the catalyst, the reaction has ended after about 70 hours.

EXAMPLE 16:

If the procedure is as in Example 4, but 10 g of potassium carbonate are employed as the catalyst, N-ethylcarbazole is obtained in the same yield with a purity of 96.5% after a reaction time of about 20 hours.

EXAMPLE 17:

If the procedure is as in Example 1, but 5 g of sodium ethylate are employed as the catalyst instead of potassium methylate at a reaction temperature of 260°–270° C., N-ethylcarbazole is obtained in a comparable yield with a purity of 95% after a reaction time of about 40 hours.

EXAMPLE 18:

87 g of carbazole, 96% pure, are melted with 0.3 g of potassium hydroxide (melting range about 245° C.) in the apparatus described in Example 1. Diethyl carbonate is added dropwise to the melt at temperatures of 245°–265° C. at a rate such that it boils constantly under reflux. In the first hours, carbazole which has sublimed at the top must be occasionally melted off. After about 20 hours, the reaction is complete and gives, after working up analogously to Example 9, N-ethylcarbazole with a purity of 96.5%.

EXAMPLE 19:

830 g of diethyl carbonate are initially introduced into a 2 l multi-necked flask with a reflux condenser which is operated with water at 90° C. and onto which a Liebig condenser operated with ice-water is mounted, and 1044 g of carbazole, 96% pure, and 40 g of potassium ethylate are introduced. The suspension is heated. At an internal temperature of about 130° C., the batch starts to boil under reflux. In the course of the reaction, the internal temperature rises and reaches 230° C. after about 4 hours. The batch is kept at 230°–240° C. for a further 24 hours, further diethyl carbonate being added at a rate such that it always boils under reflux. When the reaction has ended, the mixture is worked up as in Example 9. 1140 g of filtered product melt and a further 70 g of product from working-up the residue on the filter are obtained. Purity 95%, yield 98% of theory.

EXAMPLE 20:

47.8 g of ethyl carbazole-N-carboxylate are melted in a 100 ml flask with a reflux condenser, 1 g of potassium hydroxide and 5 g of diethyl carbonate are added and the mixture is heated to 230°–240° C., a further 10 g of diethyl carbonate being added dropwise in a manner such that diethyl carbonate constantly boils gently under reflux at an internal temperature of 230°–240° C. Carbon dioxide escapes. After 24 hours, the reaction has ended. After the diethyl carbonate has been distilled off in vacuo and the catalyst has been removed by filtration of the melt, 37 g of N-ethylcarbazole which is free from carbazole and ethyl carbazole-N-carboxylate are obtained.

EXAMPLE 21:

If the procedure is as in Example 20, but 1 g of potassium methylate is employed as the catalyst instead of potassium hydroxide at a reaction temperature of 250°–260° C., N-ethylcarbazole is obtained with a purity of 97% after a reaction time of 5 hours and customary working-up.

We claim:

1. Process for the preparation of N-ethylcarbazole of file formula I, comprising reacting a carbazole of the general formula II

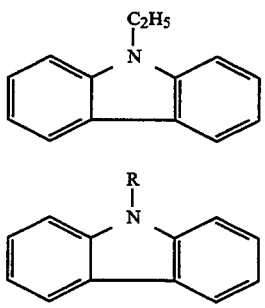

in which R denotes hydrogen or ethoxycarbonyl, with diethyl carbonate.

2. The process according to claim 1, wherein the reaction is further carried out in the presence of a catalyst.

3. The process according to claim 2, wherein the catalyst is selected from the group consisting of tertiary amines, pyridine derivatives, alkali metal salts of amines, alkali metal or alkaline earth metal salts of carbazole, alkali metal alcoholates, alkaline earth metal alcoholates or hydroxides, oxides, carbonates or phosphates of the alkali metals or alkaline earth metals or mixtures of these substances.

4. The process according to claim 2, wherein the catalyst is employed in an amount of about 0.05 to about 20 mol percent, based on the carbazole of the general formula II employed.

5. The process according to claim 3, wherein the catalyst is employed in an amount of about 0.1 to about 10 mol percent, based on the carbazole of the general formula II employed.

6. The process according to claim 1, wherein the reaction is carried out between about 130° and about 320° C.

7. The process according to claim 4, wherein the reaction is carried out between about 180° and about 300° C.

8. The process according to claim 5, wherein the reaction is carried out between about 220° and about 280° C.

9. The process according to claim 1, wherein the carbazole of the general formula II, optionally a catalyst, optionally a solvent and optionally some of the diethyl carbonate are initially introduced into a reaction vessel and the diethyl carbonate or, the remaining diethyl carbonate is metered in at the reaction temperature during the reaction.

10. The process according to claim 1, wherein the carbazole of the formula IIa

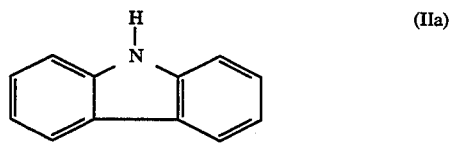

is reacted with diethyl carbonate, hydroxides, oxides, carbonates, phosphates or ethylates of alkali metals or of alkaline earth metals or the salts formed by these metals with carbazole or mixtures of these compounds being employed as the catalyst and the reaction being carried out in molten N-ethylcarbazole or in diethyl carbonate or in a mixture thereof.

11. The process according to claim 10, wherein said catalyst is potassium hydroxide, potassium carbonate or potassium ethylate or mixtures thereof.

12. The process according to claim 11, wherein the reaction is carried out between about 130° and about 320° C.

13. The process according to claim 11, wherein the diethyl carbonate is employed in an mount of about 1.1 to about 2.5 mol, based on the carbazole of the formula IIa employed.

14. The process according to claim 12, wherein the diethyl carbonate is employed in an mount of about 1.1 to about 1.8 mol, based on the carbazole of the formula IIa employed.

15. The process according to claim 1, wherein said N-ethoxycarbonylcarbazole of the formula IIb

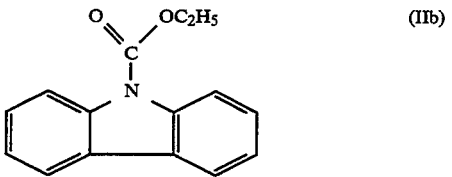

is reacted with diethyl carbonate, the diethyl carbonate being employed in an mount of about 0.1 to about 1.0 mol, based on the carbazole of the formula IIb employed and the reaction being carried out without an additional solvent.

16. The process according to claim 1, wherein said N-ethoxycarbonylcarbazole of the formula IIb

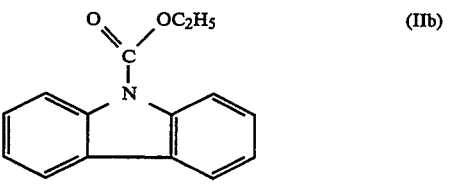

is reacted with diethyl carbonate, the diethyl carbonate being employed in an amount of about 0.3 to about 0.8 mol, based on the carbazole of the formula IIb employed and the reaction being carried out without an additional solvent.

17. The process according to claim 1, wherein the reaction is carried out at atmospheric pressure to superatmospheric pressure up to about 6 bar.

18. The process according to claim 8, wherein the reaction is carried out at atmospheric pressure to superatmospheric pressure up to about 3 bar.

* * * * *